US009289155B2

(12) United States Patent
Rigas et al.

(10) Patent No.: US 9,289,155 B2
(45) Date of Patent: Mar. 22, 2016

(54) DETECTION OF H. PYLORI UTILIZING UNLABELED UREA

(75) Inventors: Basil Rigas, Old Field, NY (US); Anastasia Rigas, Old Field, NY (US); Pelagia-Irene Gouma, Port Jefferson, NY (US); Krithika Kalyanasundaram, Longmont, CO (US)

(73) Assignee: The Research Foundation For The State University of New York, Albany, NY (US)

( * ) Notice: Subject to any disclaimer, the term of this patent is extended or adjusted under 35 U.S.C. 154(b) by 1575 days.

(21) Appl. No.: 12/678,654

(22) PCT Filed: Sep. 17, 2008
(Under 37 CFR 1.47)

(86) PCT No.: PCT/US2008/076631
§ 371 (c)(1),
(2), (4) Date: Dec. 23, 2010

(87) PCT Pub. No.: WO2009/039152
PCT Pub. Date: Mar. 26, 2009

(65) Prior Publication Data
US 2012/0034646 A1    Feb. 9, 2012

Related U.S. Application Data

(60) Provisional application No. 60/973,066, filed on Sep. 17, 2007.

(51) Int. Cl.
| C12Q 1/04 | (2006.01) |
| A61B 5/08 | (2006.01) |
| G01N 33/497 | (2006.01) |
| A61B 5/097 | (2006.01) |
| A61B 5/00 | (2006.01) |
| A61K 49/00 | (2006.01) |
| G01N 27/06 | (2006.01) |
| G01N 33/00 | (2006.01) |

(52) U.S. Cl.
CPC ............... *A61B 5/082* (2013.01); *A61B 5/097* (2013.01); *A61B 5/7282* (2013.01); *A61B 5/742* (2013.01); *A61K 49/0004* (2013.01); *C12Q 1/04* (2013.01); *G01N 33/497* (2013.01); *G01N 27/06* (2013.01); *G01N 33/0014* (2013.01); *G01N 33/0054* (2013.01)

(58) Field of Classification Search
CPC ........................................................ C12Q 1/04
See application file for complete search history.

(56) References Cited

U.S. PATENT DOCUMENTS

| 5,252,292 | A | 10/1993 | Hirata et al. | 422/98 |
| 7,014,612 | B2 | 3/2006 | Hubbard et al. | 600/532 |
| 7,017,389 | B2 | 3/2006 | Gouma | 73/1.05 |
| 7,220,387 | B2 | 5/2007 | Flaherty et al. | 422/86 |
| 2003/0217586 | A1 | 11/2003 | Gouma | 73/31.06 |
| 2005/0171449 | A1 | 8/2005 | Suslick et al. | 600/532 |

FOREIGN PATENT DOCUMENTS

WO    WO/03/041565    5/2003

OTHER PUBLICATIONS

Timmer et al. Sensors and Actuators B, 2005, 107:666-677.*
Chen et al. Chemosphere, 2005, 59:99-105.*
Kato et al. The American J of Gastroenterology, 2002, 97(7):1668-1673.*
Agilent Technologies. (Jul. 20, 2000) Material safety data sheet, Product name: Decarbite.
Kearney, D. et al. (2002) Breath Ammonia Measurement in *Helicobacter pylori* Infection, *Dig. Dis. Sci.* 47(11), 2523-2530.
Romagnuolo, J. et al. (2002) Using breath tests wisely in a gastroenterology practice: an evidence-based review of indications and pitfalls in interpretation, *The American Journal of Gastroenterology* 97(5), 1113-1126.
U.S. Appl. No. 60/973,066, Rigas, B. et al., filed Sep. 17, 2007.

* cited by examiner

*Primary Examiner* — Bin Shen
(74) *Attorney, Agent, or Firm* — Medlen & Carroll, LLP

(57) ABSTRACT

Disclosed is a method and device for detection of *H. Pylori* in breath emissions utilizing an unlabelled urea, in which a patient ingests a safe quantity of unlabelled urea. After ingestion, expired breath of the patient is analyzed for ammonia, with a detection based on levels of ammonia lower than 50 parts per billion to 500 ppm to detect *helicobacter pylori*.

6 Claims, 4 Drawing Sheets

DETECTION OF H. PYLORI UTILIZING UNLABELED UREA

PRIORITY

This application claims priority to PCT/KR2008/005262 filed Sep. 17, 2008, to U.S. Provisional Patent Application filed on Sep. 17, 2007 and assigned Ser. No. 60/973,066, the content of which is incorporated herein by reference.

BACKGROUND

1. Field of the Invention

The present invention relates generally to a medical device and protocols to facilitate diagnosis of *Helicobacter pylori* (*H. pylori*) based on administration of unlabelled urea.

2. Background of the Invention

Exhaled breath has long been known to enable non-invasive disease detection. Exhaled gases, such as ammonia, nitric oxide, aldehydes and ketones have been associated with kidney and liver malfunction, asthma, diabetes, cancer, and ulcers. Other exhaled compounds like ethane, butane, pentane, and carbon disulfide have been connected to abnormal neurological conditions. However, though analysis of body fluids (blood, sputum, urine) for disease diagnoses and monitoring is routine clinical practice, human breath analysis methodologies that exploit the non-invasive nature of such diagnoses are still under-developed and conventional technologies lack specificity, are excessively expensive or lack portability.

Sensors have been produced to measure gases in a variety of settings, including automotive and biological applications. See U.S. Pat. No. 7,017,389 to Gouma, the contents of which are incorporated by reference, regarding detection of $NO_x$ emissions in the automotive field. Technologies for monitoring exhaled breath require complex and expensive apparatuses that are difficult to calibrate and are often not sufficiently sensitive to provide a high degree of certainty in regard to medical condition diagnosis. Such biological systems pose challenges that include sensitivity to extremely low levels of gases, presence of reducing and oxidizing gases, organic vapors (VOCs), etc. See U.S. Pat. No. 7,220,387 to Flaherty et al., the contents of which are incorporated by reference, regarding disposable sensors to measure gaseous sample analytes.

A conventional apparatus disclosed by Kearney, D, et al., *Breath Ammonia Measurement in Helicobacter pylori Infection*, Digestive Diseases and Sciences, Vol. 47, No. 11, pp. 2523-2530 (2002), provides a fiber optic device placed in the stream of expelled breath that is connected to an optical sensor for detecting whether a patient has *H. pylori* by measuring for ammonia excreted by the lungs, utilizing a hydrophobic TFE-based membrane to avoid affect of dissolved ions such as ammonia. Also see, WO 03/041565 A2 of Hubbard et al., the contents of which are incorporated by reference, *H. pylori* detection.

Diagnostic tests for *H. pylori* include a) serologic testing to detect anti-*H. pylori* antibodies in blood, b) upper gastrointestinal endoscopy with mucosal biopsies, c) *H. pylori* culture, including antimicrobial susceptibility testing, and d) detection of *H. pylori* antigens in stool. Serologic testing, however, cannot distinguish current from old infection. Upper gastrointestinal endoscopic biopsies are submitted for rapid urease testing or histological examination, and this approach has the drawbacks of the invasive nature of endoscopy and the suboptimal performance of histopathology. *H. Pylori* culture is invasive and cumbersome and detection of *H. pylori* antigens in stool is limited by the low acceptance of stool testing and suboptimal specificity/sensitivity.

Several diagnostic tests are based on the ability of *H. pylori* to convert urea to CO2 and NH3 using its enzyme urease. *H. Pylori* produces large amounts of urease which often comprises about five percent of its total protein. Urease activity is assessed in two general ways: Biopsy-based rapid urease testing and various urea breath tests. Biopsy-based rapid urease tests require endoscopy for sample acquisition. Biopsy samples are placed in an agar gel or paper strip containing a pH indicator. In addition to requiring an invasive endoscopy, biopsy-based rapid urease tests provide a less-than-optimal test due to the time required for the diagnosis, which is 3-24 hours, a less than 90% specificity, and reduced sensitivity in children. Moreover, conventional devices, particularly point-of-care devices, are expensive, particularly to assess *H. pylori*, which discontinuously colonizes the gastroduodenal mucosa.

Conventional testing is performed utilizing instrumentation that ranges from variations of mass spectrometers to IR detectors that are costly and require a trained operator. Breath sample transportation is also an issue with most conventional devices. The limited availability of instruments operable by patients and available at the point of care requires samples to be shipped to central testing facilities, adding cost and inconvenience. In regard to Urea Breath Testing (UBT) for the diagnosis of *H. pylori* infection, there are two versions of the UBT, based upon the type of urea being used as a substrate: $^{13}C$ labeled urea and $^{14}C$ labeled urea. $^{14}C$ is a radioactive isotope of carbon. $^{13}C$ is a stable, non-radioactive isotope, encountered in nature. The FDA has approved both $^{13}C$- and $^{14}C$-based UBTs for the diagnosis of *H. pylori*, though the $^{14}C$-based assay is rarely used. The $^{14}C$-based UBT is associated with exposure to radioactivity, which albeit small for an otherwise healthy adult, is nevertheless present and patients should not be exposed to it in the absence of safe alternatives. It is because of the risk associated with the radioactivity of the $^{14}C$-urea that the $^{14}C$-based UBT is contraindicated in pregnant women and children. See, *Using Breath Tests Wisely in a Gastroenterology Practice: An Evidence-Based Review of Indications and Pitfalls in Interpretation*, Romagnuolo, et al., Am J Gastroenterology 97:1113-1126 (2002).

A further difficulty arising with the UBT is the high cost of $^{13}C$-urea, as well as the cost and operational expenses of instruments to detect exhaled $^{13}CO_2$.

To solve this shortcoming, the present invention departs from detection of $^{13}CO_2$ by using unlabeled urea as a substrate, detecting ammonia in breath instead of $CO_2$. The present invention provides an ammonia-specific nanosensor and provides a simple, inexpensive hand-held device for the detection of breath $NH_3$.

Accordingly, the present invention provides a highly accurate, economical, easy to operate, portable and sufficiently sensitive medical device for diagnosis of *H. Pylori*. The present invention departs from detection of $^{13}CO_2$ and provides a simplified assay that uses lower cost unlabeled urea as a substrate.

SUMMARY OF THE INVENTION

The present invention substantially solves the above shortcomings and provides at least the following advantages.

The present invention obviates the need for serologic testing, for upper gastrointestinal endoscopy with mucosal biopsies for the detection of *H. pylori*, which is invasive and cumbersome, and for detection of *H. pylori* antigens in stool.

In a preferred embodiment, a medical device is provided to sample breath emitted from a patient's mouth, to analyze ammonia content and the composition of a gaseous sample via contact with sensing electrodes, particularly gold substrates arranged on a TO8 substrate.

Another embodiment of the present invention provides a method for using the medical device of the present invention to analyze a patient's breath sample to diagnose the presence of a medical condition, by obtaining a breath sample from a patient; analyzing volatile components of the patient sample to provide a breath profile that includes both qualitative and quantitative data; comparing the patient's breath profile to a database of breath profiles, with each database profile being characteristic of at least one medical condition, to provide information pertinent to diagnosis of the presence or absence of a medical condition.

In a preferred embodiment, a single sample is used for an independent or multiple tests, which may be combined to produce a template or pattern representative of a patient's condition or representative of the presence of a particular compound or set of compounds. In a preferred embodiment high sensitivity nanomorphs of metal oxides prepared by sol-gel practices are used for a more selective and quantitatively precise analysis.

In a preferred embodiment, the invention utilizes arrays of biocomposite and bio-doped films to provide a low cost, portable analyzer for detection of chemical products of biochemical reactions, such as ammonia and NO, in a real-time manner.

DETAILED DESCRIPTION OF THE FIGURES

The above and other objects, features and advantages of certain exemplary embodiments of the present invention will be more apparent from the following detailed description taken in conjunction with the accompanying drawings, in which.

Figure 6:
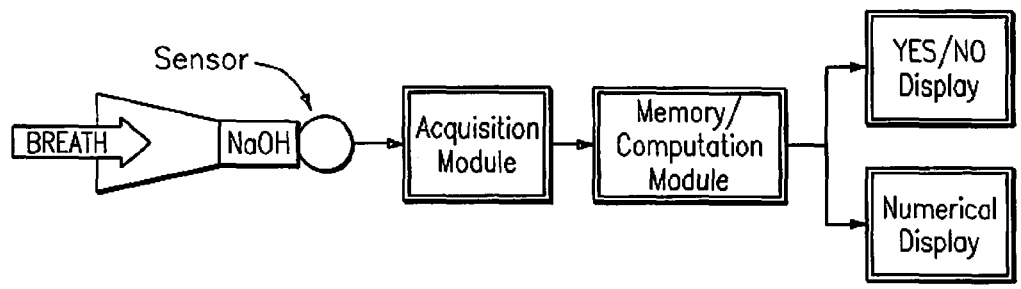

FIG. 6 provides a block diagram of an apparatus of an embodiment of the present invention.

DESCRIPTION OF THE PREFERRED EMBODIMENTS

The below description of detailed construction of preferred embodiments provides a comprehensive understanding of exemplary embodiments of the invention. Accordingly, those of ordinary skill in the art will recognize that various changes and modifications of the embodiments described herein can be made without departing from the scope and spirit of the invention. Descriptions of well-known functions and constructions are omitted for clarity and conciseness.

Figure 1:
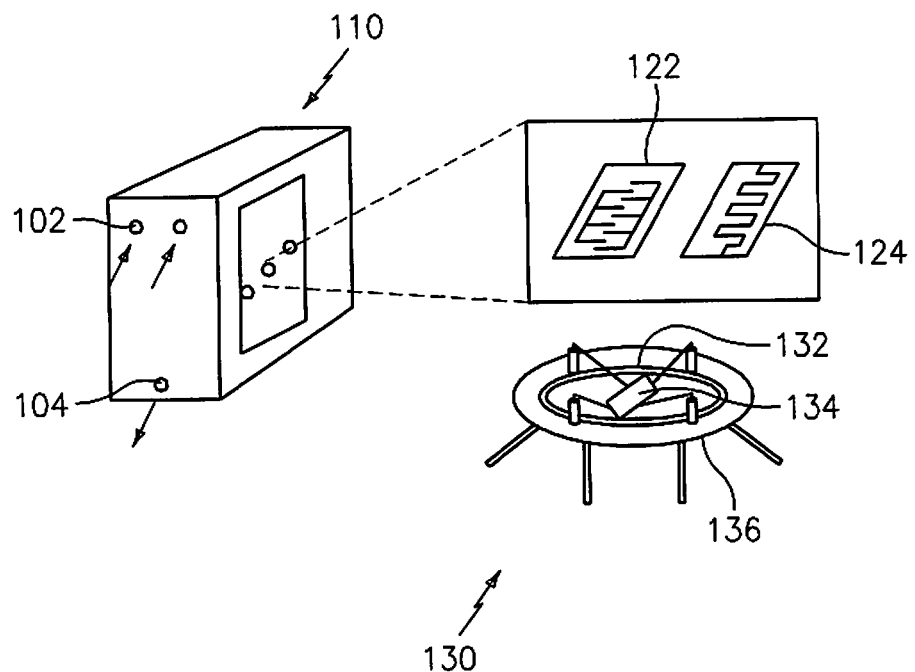
FIG. 1 is a schematic representation of an embodiment of a test device for the present invention.

Analysis of breath and skin emission samples for diagnostic purposes has the advantage that the sample to be analyzed is collected from the patient in a non-invasive manner with a minimum of discomfort or inconvenience. Basic components of the medical device used for analysis in accordance with a preferred embodiment of the present invention are shown in FIG. 1. In preferred embodiments of the invention, breath samples are quantitatively and qualitatively processed. Notably, the sensor is tuned to detect $NH_3$ levels lower than 50 parts per billion (<50 ppb) and as high as 500 ppm, thereby covering all $NH_3$ levels encountered in humans, and in particular in patients undergoing UBT. Quantitative analyzers preferably include a sensing substrate surrounded by a gold substrate surrounded by a TO8 substrate. The medical device of the present invention is preferably qualitatively used to test exhaled gas. Qualitative tests performed by the test device usable with the present invention may test carbon dioxide content, alcohol content, lipid degradation products, aromatic compounds, thio compounds, ammonia and amines or halogenated compounds.

In a preferred embodiment, multiple different tests performed on a single sample may be independent, or may be the result of several tests combined to produce a template or pattern representative of a patient's condition or representative of the presence of a particular compound or set of compounds. The high sensitivity of the nanomorphs of metal oxides prepared by sol-gel practices used in the medical device of the present invention are both more selective and more quantitatively precise than similar information obtained by currently available electronic nose technology. As a result, correlating the data pattern or changes in the data pattern over time identifies a wider range of conditions or compounds.

The present invention departs from detection of $^{13}CO_2$ and provides a simplified assay that uses unlabeled urea as a substrate and detects ammonia in breath instead of $CO_2$ utilizing Equation (1):

$$CO(NH_2)_2 + HOH\text{-urease} \rightarrow CO_2 + 2NH_3 \quad (1)$$

In an embodiment of the present invention, a nanosensor is provided to detect breath ammonia and a simple, portable, inexpensive hand-held device is thereby provided to detect breath $NH_3$. The nanosensor is tuned according to the method described below for other breath gases, and the nanosensor is in a preferred embodiment provided as a plug-in component. The sensor is constructed of a metal oxide that is not crystalline, raising sensitivity to ammonia and other gases.

Figure 2A:
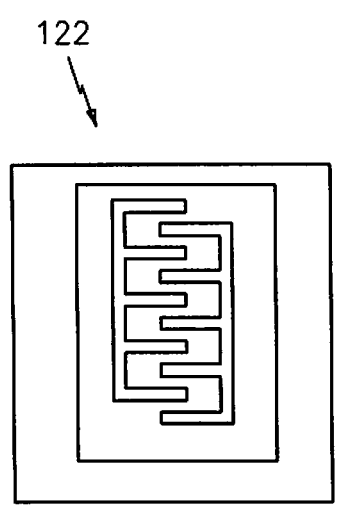
FIGS. 2a and 2b show heater and sensing electrodes utilized in FIG. 1.
Figure 2B:
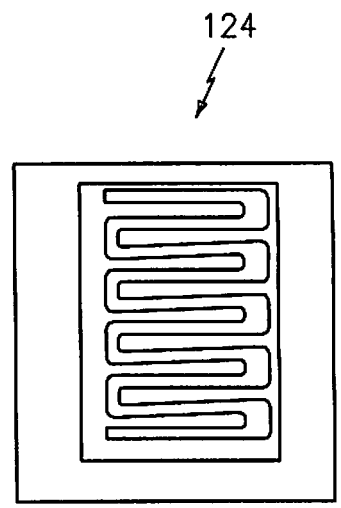

In FIG. 1, a gas sample, i.e. breath or skin emission, accesses analyzer 110 via entry and exit orifices 102 and 104. A stainless steel chamber preferably connects the orifices to avoid absorption/distortion. Sensing electrode 122 and heater electrode 124 are positioned within the analyzer 110. The sensing electrode 122 includes a sensor 130 having gold substrate 132, sensing substrate 134 and TO8 substrate 136. Heater and sensing electrodes 122 and 124 of an embodiment of the present invention are shown in FIGS. 2a and 2b. Those of skill in the art recognize use of the TO8 substrate. Hirata et al. in U.S. Pat. No. 5,252,292, the contents of which are incorporated by reference herein, disclose a type of ammonia sensor.

In the present invention, the sensing electrode 124 is selectively tuned by spin or drop coating of sensing substrates generating a film of $MoO_3$. In a preferred embodiment, a gel-sol synthesis was employed to produce three-dimensional (3-D) networks of nanoparticles, with the sol-gel processing preparing a sol, gelating the sol and removing the solvent. Molybdenum trioxide (MoO3) was prepared by an alkoxide reaction with alcohol according to Equation (2):

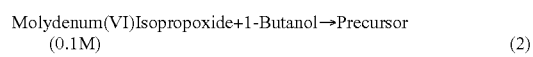

$$\text{Molydenum(VI)Isopropoxide} + \text{1-Butanol} \rightarrow \text{Precursor (0.1M)} \quad (2)$$

The prepared sol was spin coated and drop coated onto sensing substrates generating thin films of $MoO_3$. The sensing substrates (3 mm×3 mm) were made of $Al_2O_3$ and were patterned with interdigitated Pt electrodes. Pt heater electrodes were embedded on the rear of the sensor. The amorphous films were then calcined at higher temperatures generating polymorphic form. Differential scanning calorimetry confirmed the phase transformation.

Figure 3B:
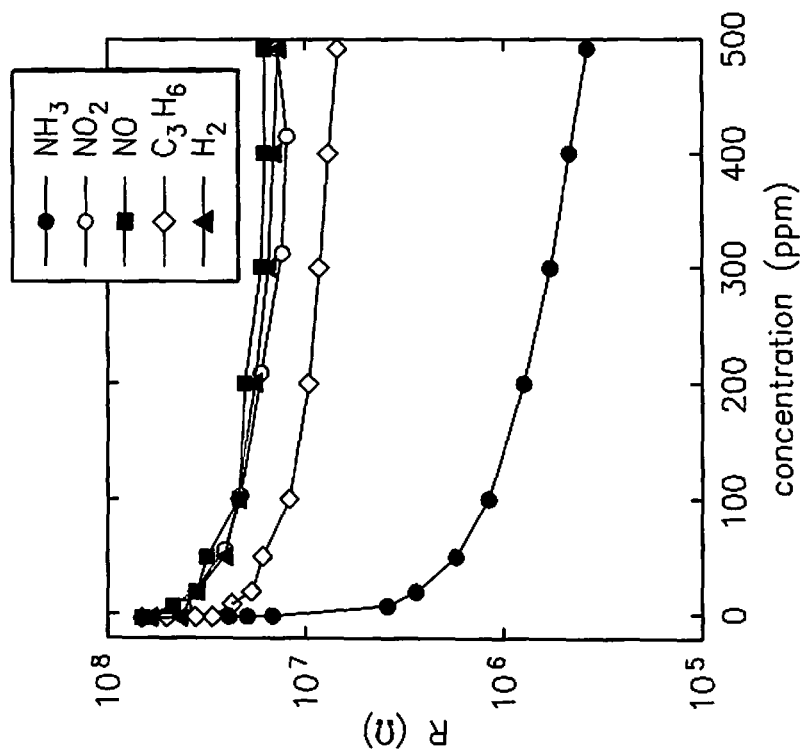
FIGS. 3a and 3b show sensor response of the test device of FIG. 1.
Figure 3A:
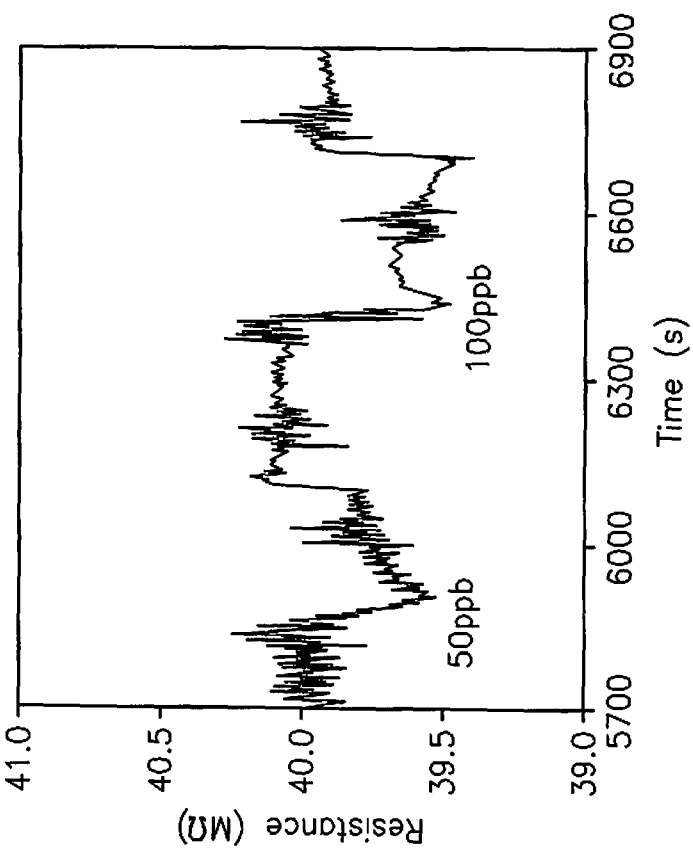

FIG. 3a shows sensor response to $NH_3$, with the sensor generating a clear and measurable response to two $NH_3$ concentrations, 50 and 100 ppb. The measured amounts of ppb, i.e. parts per billion, are much lower than amounts typically expected in human breath, allowing for more accurate and expedited measurement and results. FIG. 3b shows sensor response to various breath gases, and the specificity regarding same. Shown in FIG. 3b are $NH_3$, $NO_2$, NO, $C_3H_6$ and $H_2$, gases that potentially interfere with $NH_3$ determination.

Figures 4A, 4B:
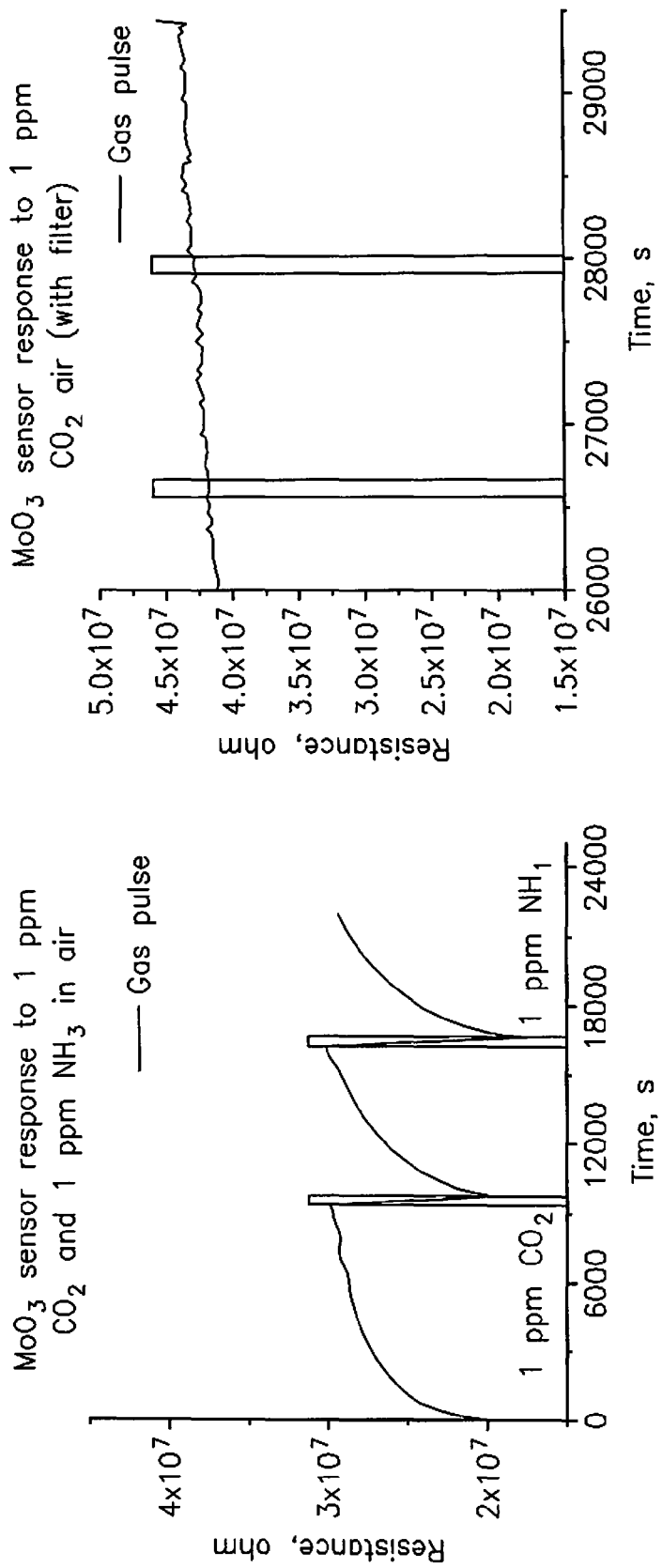
FIGS. 4a and 4b show $NH_3$ sensing and sensor response when exposed only to $CO_2$.

FIG. 4a shows $NH_3$ sensing without a $CO_2$ filter, as gas-sensing properties of the nanosensor. As shown in FIGS. 4a-b, when the sensor was exposed to various concentrations of $NH_3$ gas in a background mixture of $N_2$ and $O_2$ simulating ambient air, $NH_3$ was detected easily, down to 50 ppb, and even lower concentrations.

In FIG. 4a, $CO_2$ and $NH_3$, each at 1 ppm, produce similar responses to gas pulses, shown as vertical lines in FIG. 4a. Sensor response when exposed only to $CO_2$ gas, in the presence of the $CO_2$ filter, is shown in FIG. 4b. The $CO_2$ filter completely eliminates $CO_2$ from the gas stream, abrogating the sensor response to it.

Sensor specificity, in regard to sensing of $NH_3$, was evaluated by exposing the sensor to various gases typically encountered in human breath, including $NO_2$, NO, $C_3H_6$, and $H_2$, each up to 490 ppm. Conductivity changes were measured in dry $N_2$ with 10% $O_2$. At 440° C. the film was very sensitive to $NH_3$, with 490 ppm increasing the conductivity by approximately a factor of 70, approximately 17 times greater than the response to the other gases. The $NH_3$ response, however, was relatively unaffected by 100 ppm of $NO_2$, NO, $C_3H_6$, and $H_2$. X-ray photoelectron spectroscopy (XPS) showed that the increased conductivity in the presence of $NH_3$ was accompanied by a partial reduction of the surface $MoO_3$. The resistance of the films increased after extended time at elevated temperatures.

$CO_2$ is an important component of human breath, with its concentration in expired breath reaching up to 5%. Under test conditions, $CO_2$ interfered with $NH_3$ sensing. To overcome this limitation, a commercially available $CO_2$ filter (NaOH premixed with Vermiculite (V-lite) used in a 10:1 ratio; Decarbite absorption tube, PW Perkins and Co) was used. Decarbite reacts only with highly acidic gases such as $CO_2$, $H_2S$, thus excluding the possibility of cross adsorption; and the latter was verified. Exposing the sensor to various concentrations of $NH_3$ and $CO_2$, in the presence of $N_2$ and $O_2$, indicated that the presence of $CO_2$ did not affect $NH_3$ sensing. This was found to be true even when the two gases were at equal concentrations ranging between 0.5 and 10 ppm.

The data shown in FIGS. 4a-b are from experiments with a low $CO_2$ concentration (1 ppm). In the present invention, the NaOH Decarbite traps $CO_2$ more efficiently at high $CO_2$ concentrations.

Figure 5:
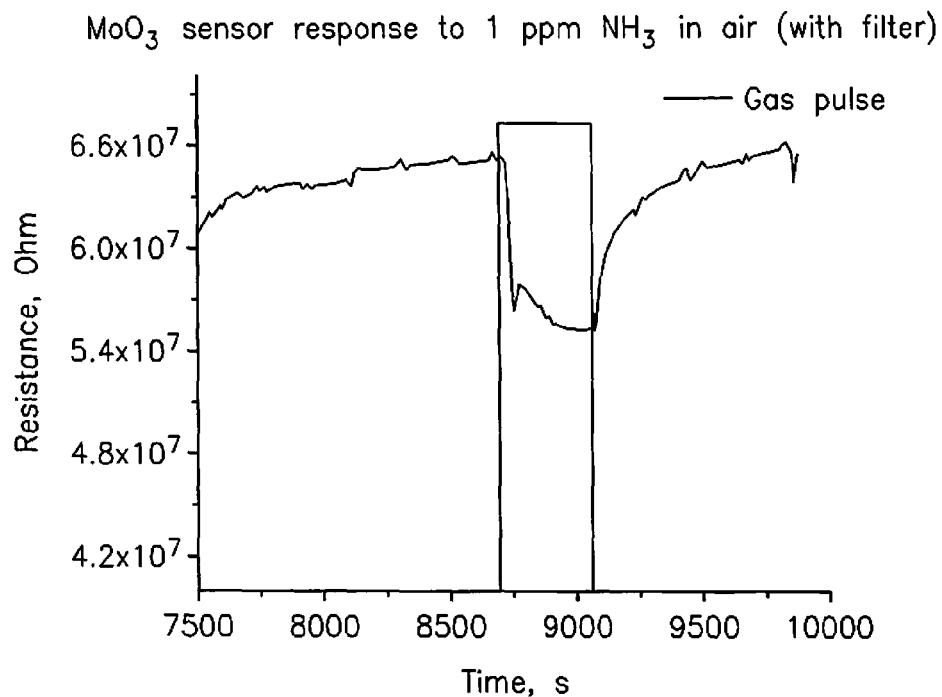
FIG. 5 shows $NH_3$ sensing with a $CO_2$ filter.

FIG. 5 shows $NH_3$ sensing with a $CO_2$ filter. In FIG. 5, the sensor is exposed to $NH_3$ in the presence of the filter, with no interference of the measurement. FIG. 6 shows a prototype for sensing breath, having a sensor, acquisition module, memory/computation module and displays.

Combining $NH_3$ and $CO_2$ generated similar results, with the filter eliminating the experimental 1 ppm of $CO_2$ in the gas stream. Even at low concentrations, interference by $CO_2$ is eliminated. Operation of the apparatus of the present invention is preferably based on sensor response modifying electrical resistance. That is, the $MoO_3$ sensor is prepared with properties required for its intended use, with lower limits of detection for $NH_3$ well below the $NH_3$ concentrations typically found in human breath and, of course, below the increased $NH_3$ levels of a positive UBT.

Another embodiment includes colloidal synthesis of hexagonal $WO_3$ nanowire and sheets. Lithium ion batteries are vital for advancing the field of portable electronics. They operate by reversibly inserting Li+ ions from the electrolyte into the electrodes and for generating electricity. Reversible intercalation of Li+ ions into the host matrix is crucial for battery operation and can be accomplished by having electrode materials that have relatively open crystal structures. Thermodynamically stable crystal structures are typically close-packed, to whereas metastable oxide phases have open lattices that promote very high diffusion rates for intercalating ions.

Building smaller and more efficient batteries is imperative for advancing nanoelectronics. The synthesis of novel materials with reduced dimensionalities for battery electrodes is the key factor in improving battery performance. One-dimensional nanomaterials with high aspect ratio such as nanowires are used to construct miniaturized power units and to increase the surface area of the electrodes in order to increase energy density. Building 3-dimensional architectures of micro-/nano electrodes allows for a reduced footprint area for the battery, while at the same time the high aspect ratio of the nanowires serves to increase the energy density tremendously.

In the area of resistive gas sensing, the attraction of hexagonal $WO_3$ lies in the structural similarity it shares with the orthorhombic form of $MoO_3$. Both these crystal structures have layered oxygen octahedra, in other words an open lattice structure, that provides long paths for small, diffusing gas molecules and facilitates easy removal of oxygen ions from the lattice. The present invention utilizes the key role played by the crystal structure in determining selectivity of the sensing matrix. Orthorhombic $MoO_3$ has been shown to be selective to ammonia in the presence of other gases. $MoO_3$ with its low sublimation temperature is not a suitable candidate for prolonged use at elevated temperatures. $WO_3$ on the other hand has higher structural integrity than $MoO_3$ and hence ideal for high temperature sensor applications. Also the high aspect ratio of the nanowires will serve to improve the energy density of the batteries without increasing the effective volume of the battery.

Also, metal oxides with lower dimensionalities have been the focus of intense research activity for applications requiring high surface-area to volume ratio such as gas sensing.

Nanowires of h-$WO_3$ are fabricated by hydrolysis and subsequent annealing of a sub-stoichiometric metal alkoxide precursor (tungsten (V) isopropoxide-W (i Pr)5) in air at a maximum temperature limit of 515° C. The sol-gel reaction occurring with the metal alkoxide precursor is outlined in Equation (3):

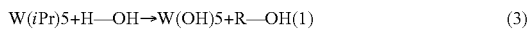

$$W(iPr)5+H—OH \rightarrow W(OH)5+R—OH(1) \quad\quad (3)$$

The hydrolysis and subsequent condensation occur by alcoxolation, i.e. by removal of water. The isopropoxide functional group is removed as isopropanol, which then dries out. The precursor for the hexagonal lattice requires an additive for stabilizing the framework. The substoichiometric isopropoxide precursor on reaction with atmospheric moisture results in the formation of H0.24$WO_3$ that is known to transform to h-$WO_3$ on oxidation in air. The metal alkoxide is sub-stoichiometric and removal of two molecules of water from the W(OH)5 in Equation (3) results in a lone hydrogen atom that can be accommodated in the interstitial spaces of $WO_3$ framework.

Advantages of this embodiment include single step synthesis of a novel metastable phase of $WO_3$; unique crystal structure of the material enables reversible intercalation of Li ions for rechargeable batteries; higher thermal stability; high aspect ratio nanostructures such as nanowires, nanocubes and nanosheets for high surface area to volume ratio applications.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for detection of *Helicobacter pylori*, the method comprising: ingesting by a patient a safe quantity of unlabelled urea; and analyzing, after the ingestion and after removal of $CO_2$, expired breath of the patient for ammonia with a sensor constructed of a metal oxide, wherein the analysis is based on levels of ammonia lower than 50 parts per billion to 500 ppm to detect *helicobacter pylori*.

2. The method of claim 1, wherein the detection is not based on $^{13}CO_2$ levels.

3. The method of claim 1, wherein the analysis is based on an equation:

$$CO(NH_2)_2 + HOH\text{-urease} > CO_2 + 2NH_3.$$

4. The method of claim 1, wherein the removal of $CO_2$ is performed with a $CO_2$ trap.

5. The method of claim 4, wherein the $CO_2$ trap is a NaOH trap.

6. The method of claim 1, wherein the patient is a pediatric patient.

* * * * *